US009775679B2

(12) United States Patent
Eschborn et al.

(10) Patent No.: US 9,775,679 B2
(45) Date of Patent: Oct. 3, 2017

(54) ADAPTER IDENTIFICATION OF A REPROCESSING DEVICE FOR SURGICAL INSTRUMENTS

(71) Applicant: OLYMPUS WINTER & IBE GMBH, Hamburg (DE)

(72) Inventors: Sascha Eschborn, Ahrensburg (DE); Benjamin Ottens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 114 days.

(21) Appl. No.: 14/687,160

(22) Filed: Apr. 15, 2015

(65) Prior Publication Data

US 2015/0216608 A1 Aug. 6, 2015

Related U.S. Application Data

(63) Continuation of application No. PCT/EP2013/003005, filed on Oct. 7, 2013.

(30) Foreign Application Priority Data

Oct. 16, 2012 (DE) .......................... 10 2012 218 811

(51) Int. Cl.
 *B08B 3/00* (2006.01)
 *A61B 19/00* (2006.01)
 (Continued)

(52) U.S. Cl.
 CPC .......... *A61B 19/34* (2013.01); *A61B 1/00059* (2013.01); *A61B 1/00128* (2013.01);
 (Continued)

(58) Field of Classification Search
 CPC ... B08B 9/0325; A61B 19/34; A61B 1/00059; A61B 1/00128; A61B 1/125;
 (Continued)

(56) References Cited

U.S. PATENT DOCUMENTS

| 4,637,378 A | 1/1987 | Sasa |
| 2002/0161460 A1 | 10/2002 | Noguchi |

(Continued)

FOREIGN PATENT DOCUMENTS

| CN | 101111322 A | 1/2008 |
| CN | 101600386 A | 12/2009 |

(Continued)

OTHER PUBLICATIONS

International Search Report dated Feb. 4, 2014 issued in PCT/EP2013/003005.

(Continued)

*Primary Examiner* — Eric Golightly
(74) *Attorney, Agent, or Firm* — Scully, Scott, Murphy & Presser, P.C.

(57) ABSTRACT

An adapter device for use in a reprocessing device for reprocessing surgical instruments. The adapter device including: at least one first fluid attachment, on an inlet side for connection to a coupling device of the reprocessing device; at least one second fluid attachment, on an outlet side for connection to the surgical instrument, the at least one second fluid attachment being adapted geometrically to an attachment of the surgical instrument; and an adapter identification feature that is detectable by the reprocessing device. Also provided is a reprocessing system having a reprocessing device for reprocessing surgical instruments and having the adapter device. The reprocessing device including: the coupling device for connecting to the adapter device; and a detection device which detects, with the adapter device connected to the reprocessing device, the adapter identification feature of the adapter device.

12 Claims, 1 Drawing Sheet

(51) Int. Cl.
*A61B 1/00* (2006.01)
*A61B 1/12* (2006.01)
*F16L 21/00* (2006.01)
*A61B 90/96* (2016.01)
*A61B 90/70* (2016.01)
*A61B 90/98* (2016.01)

(52) U.S. Cl.
CPC .............. *A61B 1/123* (2013.01); *A61B 1/125* (2013.01); *A61B 90/70* (2016.02); *A61B 90/96* (2016.02); *A61B 90/98* (2016.02); *F16L 21/00* (2013.01); *A61B 2090/701* (2016.02); *F16L 2201/60* (2013.01)

(58) Field of Classification Search
CPC ......... A61B 90/96; A61B 90/70; A61B 90/98; A61B 1/123; A61B 2090/701; A61B 2019/343; F16L 21/00; F16L 2201/60
USPC ............................................ 134/113; 285/93
See application file for complete search history.

(56) References Cited

U.S. PATENT DOCUMENTS

| | | |
|---|---|---|
| 2006/0102200 A1 | 5/2006 | Esquenet et al. |
| 2008/0267688 A1 | 10/2008 | Busted |
| 2009/0220377 A1 | 9/2009 | Hasegawa et al. |
| 2011/0097248 A1 | 4/2011 | Tomita et al. |
| 2011/0196291 A1 | 8/2011 | Vischer et al. |

FOREIGN PATENT DOCUMENTS

| | | |
|---|---|---|
| DE | 102009036564 A1 | 2/2011 |
| JP | 2009-131296 A | 6/2009 |
| JP | 2009-136492 A | 6/2009 |
| JP | 2009-172013 A | 8/2009 |

OTHER PUBLICATIONS

Japanese Office Action dated Mar. 14, 2017 in Japanese Patent Application No. 2015-537159.

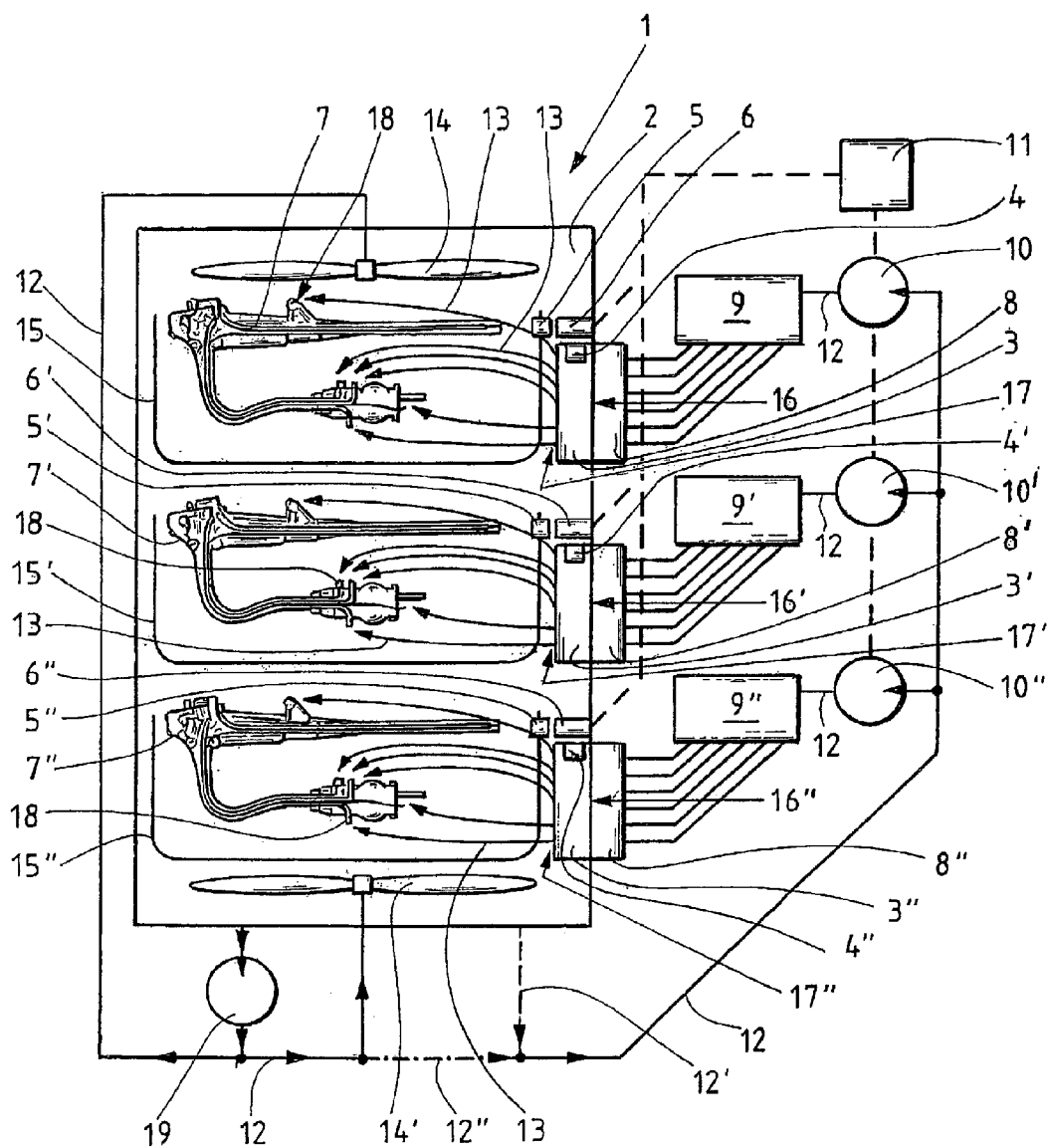

ADAPTER IDENTIFICATION OF A REPROCESSING DEVICE FOR SURGICAL INSTRUMENTS

CROSS-REFERENCE TO RELATED APPLICATION

The present application is a continuation of PCT/EP2013/003005 filed on Oct. 7, 2013, which is based upon and claims the benefit of DE 10 2012 218 811.8 filed on Oct. 16, 2012, the entire contents of each of which are incorporated herein by reference.

BACKGROUND

Field

The present application relates to an adapter device for use in a reprocessing device for reprocessing surgical instruments, in particular endoscopes, wherein the adapter device is provided, on its inlet side, with at least one fluid attachment for connection to a coupling device of the reprocessing device, while its outlet side is provided with at least one fluid attachment which serves for connection to the surgical instrument and is adapted geometrically to an attachment of the surgical instrument. The present application also relates to a reprocessing system having a reprocessing device for reprocessing surgical instruments, in particular endoscopes, and having an adapter device, wherein the reprocessing device has a coupling device for connection, in particular attachment, to an adapter device comprised by the reprocessing system. Finally, the present application relates to a method for operating a reprocessing system comprising at least one adapter device.

Prior Art

Reprocessing devices of surgical instruments, in particular of endoscopes, usually have systems, or respectively devices, which clean and disinfect both the outer surfaces of the surgical instrument as well as the channels, or respectively channel systems, of the same. Rinsing circuits are usually provided for this purpose. In particular, with rinsing the inner channel of a surgical instrument, in particular of an endoscope, or respectively a flexible endoscope, the hygienic result of the reprocessing depends on the flow quantity, the size of which is limited by the maximum rinsing pressures permissible for the respective surgical instrument. These maximum permissible rinsing pressures are determined variously by different manufacturers of surgical instruments. These range, for example from 0.8 bar differential pressure with a few manufacturers, to 2.0 bar differential pressure, with the applicant.

The rinsing circuits for reprocessing the channels, or respectively channel systems, of surgical instruments, in particular flexible endoscopes, are preferably designed to a highest possible flow. However, the permissible flow is defined here using the surgical instrument with the smallest permissible pressure that is compatible with the reprocessing device, or respectively the reprocessing system.

Because the reprocessing devices, or respectively reprocessing systems, are suitable for various surgical instruments, with endoscopes having a higher approved pressure of the fluid, or respectively with a higher permissible fluid pressure, this results in a poor hygienic result, or respectively the corresponding surgical instrument must be treated longer to obtain a good hygienic result. This is due to the fact that the reprocessing device, or respectively the reprocessing system is designed for a pressure, which is based on the respective surgical instrument that tolerates the lowest maximum pressure.

SUMMARY

An object is to specify a reprocessing system, and an adapter device for the system, and a method for operating a reprocessing system by means of which an optimal and efficient cleaning is possible even with different surgical instruments.

This object is solved by an adapter device for use in a reprocessing device for reprocessing surgical instruments, in particular endoscopes, wherein the adapter device on the inlet side has at least one fluid attachment for connection to a coupling device of the reprocessing device, and the outlet side has at least one fluid attachment which serves for connection to the surgical instrument and is adapted geometrically to an attachment of the surgical instrument, which is further developed in that the adapter device has an adapter identification feature that is detectable by the reprocessing device.

By using the adapter device according to the invention in a reprocessing device for reprocessing surgical instruments, it is possible to quickly detect which surgical instrument is to be cleaned, so that the fluid pressure can be adjusted to the respective surgical instrument, such that it is possible to obtain excellent hygienic results in a relatively short time.

Here, it is considered in particular, that in particular, with the surgical instrument a plurality of channels are present, the attachment of which, or respectively channel attachment of which, has different geometries so that a unique assignment is possible to the surgical instruments, or respectively to the surgical instrument. Here it is preferably provided that the end pieces of the fluid attachments of the adapter device, or respectively the end piece of the fluid attachment of the adapter device, fits with only one type of surgical instrument, or respectively the channel attachments, in order to provide a unique assignment of an adapter device to a surgical instrument. An exchange of the adapter device is excluded due to the mechanical coding of the fluid attachments, or respectively the fluid attachment, and the counter piece to this provided on the channel of the surgical instrument. According to the invention, the adapter device is additionally provided with an adapter identification feature, by means of which the reprocessing device can detect which adapter device is in use so that the correct pressure which should be provided for rinsing the surgical instrument can be made available for the reprocessing device, or respectively in the reprocessing device.

The adapter identification feature preferably comprises an RFID transponder, a bar coding and/or a magnetic coding. Here it is particularly preferred to provide an RFID transponder in, or respectively on, an adapter device. The adapter device, when it is arranged in a rinsing space of the reprocessing device, can then be detected, or respectively identified, by means of an RFID reader device which is comprised by the reprocessing device. This information can then be used subsequently in order to adjust the ideal rinsing pressure for the surgical instrument attached to the adapter device. An eminent advantage here, is that using the adapter identification feature guarantees the information is always present about which adapter device, which is designed for example as an adapter plate, is connected to the reprocessing device. Hereby, it can be excluded here that an unknown adapter device is attached, which allows a clear advantage in the identification of surgical instruments and for the rinsing pressure to be provided for this purpose. In addition then, the adapter device used for the reprocessing can also be noted in a reprocessing log, which allows a complete documentation of the reprocessing of the surgical instruments.

Instead of an RFID technology, other forms of detecting the adapter device can also be provided. A bar coding or a magnetic coding could be provided for example.

The object is further solved by a reprocessing system comprising the following features:

a reprocessing device for reprocessing surgical instruments, in particular endoscopes, and an adapter device are provided, wherein the reprocessing device has a coupling device for connecting, in particular attaching, to the adapter device. In addition, a detection device is provided which, in particular with an adapter device attached to the reprocessing device, or respectively with an adapter device connected to the reprocessing device, detects the adapter identification feature of the adapter device.

Here, the detection device is preferably arranged on, in or in proximity of the coupling device. The reprocessing device is attached, in particular as a fluid attachment, to the adapter device using the coupling device.

An RFID reader device, a bar code reader device, and/or a magnetic field detection device or devices are provided. Here, due to cost considerations, it is preferable to provide only one of the detection devices, thus, either an RFID reader device, a barcode reader device, or a magnetic field detection device. However, two or more of these detection devices can also be provided in order to allow a very secure detection of the adapter device.

A plurality of coupling devices are provided, each of which can be connected or is connected to an adapter device or a plurality of adapter devices. Hereby, a plurality, in particular also different, surgical instruments can be connected to the reprocessing device using the respective adapter device which makes the reprocessing system extremely efficient.

A pump that can be controlled or regulated is provided in the reprocessing device for each adapter device provided in the reprocessing device. Hereby, different fluid pressures can be supplied efficiently to different surgical instruments.

A basket for supporting a surgical instrument in the reprocessing device is provided, wherein the basket has a basket identification feature that can be detected by the reprocessing device, in particular, that can be detected or is detected by the detection device of the reprocessing device. Thus, the system comprises a basket in which a surgical instrument is supported or can be accommodated. The basket has a basket identification feature with which it is possible to identify to the adapter device, the basket according to the identification feature, and thus also a surgical instrument inserted in the basket. Here, preferably the same detection device can be used for detecting the basket identification feature as that which detects also the adapter identification feature.

The basket identification feature can comprise an RFID transponder, a bar coding or a magnetic coding. In this case also, the RFID transponder is particularly preferred. For this case, an RFID reader device serves as a detection device which in particular detects both the RFID transponder of the basket as well as the RFID transponder of the adapter device. The information, which basket is inserted or will be inserted in connection to an adapter device in the reprocessing device, can be used in addition to documentation purposes, also in order to release specific baskets only for specific reprocessing programs. This can be expedient, for example, if the reprocessing device, or respectively the reprocessing system, also offers the possibility of a thermal reprocessing. Hereby, damage to flexible endoscopes due to high temperatures as well as damage to further surgical instruments, for instance due to chemicals, can be excluded.

The object is further solved by a method for operating a reprocessing system, described above, comprising at least one adapter device, described above, having the following method steps:

attaching or connecting a surgical instrument to the adapter device, detecting the adapter device using a detection device provided in the reprocessing device, attaching or connecting the adapter device on its inlet side to the reprocessing device, and setting a fluid pressure depending on the detection of the adapter device by a control or regulation device of the reprocessing device.

Due to the method according to the invention, it is possible to treat surgical instruments very efficiently.

At least one channel of the surgical instrument can be rinsed with fluid at the set fluid pressure. It is particularly preferred when a plurality of adapter devices are connected, or respectively attached, to the reprocessing device and an individual fluid pressure is set for each adapter device. Different surgical instruments can be treated then, for example rinsed, by means of the individual fluid pressure.

Further characteristics of the invention will become apparent from the description of the embodiments according to the invention together with the claims and the included drawings. Embodiments according to the invention can fulfill individual characteristics or a combination of several characteristics.

BRIEF DESCRIPTION OF THE DRAWINGS

The invention is described below, without restricting the general idea of the invention, based on exemplary embodiments with reference to the drawing, whereby we expressly refer to the drawing with regard to the disclosure of all details according to the invention that are not explained in greater detail in the text. It shows in:

The FIGURE illustrates a reprocessing system according to an embodiment of the invention, shown schematically.

DETAILED DESCRIPTION

In the FIGURE, the same or similar types of elements and/or parts are provided with the same reference numbers so that a corresponding reintroduction can be omitted.

The FIGURE schematically shows a reprocessing system 1 that comprises a reprocessing device 2. The reprocessing device 2 has sufficient space, or respectively room, in order to receive three endoscopes 7, 7', 7" supported in baskets 15, 15', 15" provided therefor. The endoscopes have appropriate channels, which are to be rinsed. For this purpose, the endoscopes are connected to tubes 13 which are to be attached to different endoscope attachments 18. The endoscope attachments 18 are each mechanically coded differently depending on each channel, or respectively for each type of endoscope and also possibly depending on the manufacturer of an endoscope, such that the respective tubes 13 with the end pieces thereof, not shown, fit precisely on the channel inlets.

In this example embodiment, six tubes 13, which are to be attached appropriately, are provided for each endoscope. The tubes 13 are attached to the outlet sides 17, 17', 17" of the adapter device 3, 3', 3". The adapter devices 3, 3', 3" are each connected at the inlet sides 16, 16', 16" of the adapter device 3, 3', 3" to a coupling device 8, 8', 8" of the reprocessing device 2.

The adapter devices 3, 3' and 3" each have an RFID transponder 4, 4', 4". The RFID transponders 4, 4', 4" each comprise information about the respective adapter device 3, 3', 3", which can be read using the RFID reader devices 6, 6', 6". The signal strengths is or will be adjusted such that only the signals, or respectively information of the RFID transponders assigned to the respective RFID reader device will be read by the reader device assigned to the transponder.

Corresponding fluid lines, which originate from a fluid distributor 9, 9', 9" lead to the coupling devices 8, 8', 8". Fluid with appropriate fluid pressures is distributed in the respective fluid distributor 9, 9', 9". This fluid arrives, via the attached lines, through the coupling devices 8, 8', 8" via the respective adapter devices 3, 3' and 3" into the tubes 13.

Different pressures can be set using the pumps 10, 10' and 10". A control or regulation device 11 (commonly referred to in the claims as a control device) serves for this purpose, receiving appropriate signals via the signal lines, shown by dotted lines, from the reader devices 6, 6', and 6". These signals are further processed accordingly. An assignment to the respective surgical instrument occurs such that the pressure suited for the respective surgical instrument 7, 7' and 7" is set by means of the pumps 10, 10' and 10".

A rinsing circuit is used for rinsing the channels of the endoscope 7, 7', 7". The rinse fluid, as mentioned is, on the one hand conveyed through the channels of the endoscope, and on the other hand is projected, or respectively sprayed from the outside onto the endoscope, namely via fluid distributors 14 and 14', which can be mounted rotatingly.

The respective rinsing circuit is designed such that rinsing fluid is removed out of the wash compartment of the reprocessing device 2 by means of the circulation pump 19, and is supplied to the fluid distributors 14 and 14'. For the case of non-self-priming pumps 10, 10' and 10", the line 12" is provided, by means of which the rinsing fluid is then supplied to the pumps 10, 10', and 10". In this case, the line 12' is omitted. A line 12' is provided for the case that the pumps 10, 10', 10" are self-priming pumps. The line 12" is then omitted. In this case, the pumps 10, 10' and 10" automatically suction rinsing fluid out of the wash area of the reprocessing device 2.

In addition, the corresponding baskets 15, 15', and 15" can have an RFID transponder 5, 5', 5", so that it is possible to uniquely identify the respective basket.

Instead of RFID transponders and an RFID reader unit, or respectively an RFID reader device, other detection devices can also be used, as was already mentioned above.

All named characteristics, including those taken from the drawings alone, and individual characteristics, which are disclosed in combination with other characteristics, are considered individually and in combination as essential to the invention. Embodiments according to the invention can be satisfied through individual characteristics or a combination of several characteristics.

LIST OF REFERENCE SYMBOLS

1 reprocessing system
2 reprocessing device
3, 3', 3" adapter device
4, 4', 4" RFID transponder
5, 5', 5" RFID transponder
6, 6', 6" reader device
7, 7', 7" endoscope
8, 8', 8" coupling device
9, 9', 9" fluid distributor
10, 10', 10" pump
11 control or regulation device
12, 12', 12" line
13 tube
14, 14', fluid distributor
15, 15', 15" basket
16, 16', 16" inlet side
17, 17', 17" outlet side
18 endoscope attachment
19 circulation pump

What is claimed is:

1. An adapter device for use in a reprocessing device for reprocessing a plurality of types of surgical instruments, the adapter device comprising:
    at least one first fluid attachment, on an inlet side, the at least one first fluid attachment being configured to be connected to a coupling device of the reprocessing device;
    at least one second fluid attachment, on an outlet side, the at least one second fluid attachment being adapted geometrically to be uniquely connectable to an attachment of one type of surgical instrument of the plurality of types of surgical instruments; and
    an adapter identification feature configured to be detectable by the reprocessing device.

2. The adapter device according to claim 1,
    wherein the adapter identification feature comprises one of an RFID transponder, a bar coding and a magnetic coding.

3. A reprocessing system comprising:
    the adapter device according to claim 1;
    the reprocessing device for reprocessing the plurality of types of surgical instruments, wherein the reprocessing device comprises:
        the coupling device configured to be connected to the adapter device; and
        a detection device configured to detect, with the adapter device connected to the reprocessing device, the adapter identification feature of the adapter device.

4. The reprocessing system according to claim 3,
    wherein the detection device comprises one or more of an RFID reader device, a barcode reader device and a magnetic field detection device.

5. The reprocessing system according to claim 3,
    wherein the coupling device comprises a plurality of coupling devices,
    wherein the adapter device comprises a plurality of adapter devices, and
    wherein each of the plurality of coupling devices is configured to be connected to a corresponding one of the plurality of adapter devices.

6. The reprocessing system according to claim 3,
    wherein the adapter identification feature is configured to uniquely identify the one type of surgical instrument of the plurality of types of surgical instruments, and
    wherein the reprocessing device further comprises:
        a pump configured to pump a fluid to the one type of surgical instrument via the coupling device and the adapter device; and
        a controller configured to:
            set a pressure at which the pump pumps the fluid to the one type of surgical instrument via the coupling device and the adapter device based on the adapter identification feature that uniquely identifies the one type of surgical instrument of the plurality of types of surgical instruments; and control the pump to pump the fluid at the pressure set.

7. The reprocessing system according to claim 3, further comprising a basket configured to support the one type of surgical instrument in the reprocessing device, wherein the basket comprises a basket identification feature configured to be detectable by the reprocessing device.

8. The reprocessing system according to claim 7, wherein the basket identification feature comprises one of an RFID transponder, a bar coding and a magnetic coding.

9. A method for operating a reprocessing system comprising:

a reprocessing device for reprocessing a plurality of types of surgical instruments, wherein the reprocessing device comprises a coupling device;

an adapter device comprising:

at least one first fluid attachment, on an inlet side, the at least one first fluid attachment being configured to be connected to the coupling device of the reprocessing device;

at least one second fluid attachment, on an outlet side, the at least one second fluid attachment being adapted geometrically to be uniquely connectable to an attachment of one type of surgical instrument of the plurality of types of surgical instruments; and an adapter identification feature configured to be detectable by the reprocessing device, wherein the reprocessing device further comprises:

a detection device configured to detect, with the adapter device connected to the reprocessing device, the adapter identification feature of the adapter device, wherein the method comprises:

connecting the one type of surgical instrument to the at least one second fluid attachment of the adapter device;

detecting the adapter identification feature of the adapter device by the detection device of the reprocessing device;

connecting the at least one first fluid attachment of the adapter device at the inlet side to the coupling device of the reprocessing device; and setting a fluid pressure of fluid to be pumped through the coupling device, the at least one first fluid attachment of the adapter device, the at least one second fluid attachment of the adapter device and the attachment of the one type of surgical instrument, depending on the adapter identification feature of the adapter device by a control device.

10. The method according to claim 9, further comprising rinsing at least one channel of the one type of surgical instrument with the fluid at the set fluid pressure.

11. The method according to claim 9, wherein the connecting of the adapter device to the coupling device comprises connecting a plurality of the adapter device to the reprocessing device, and wherein the setting the fluid pressure comprises setting an individual fluid pressure for each of the plurality of the adapter device.

12. The reprocessing system according to claim 7 wherein the basket identification feature is configured to be detected by the detection device of the reprocessing device.

* * * * *